United States Patent [19]

Hokama

[11] 4,402,729
[45] Sep. 6, 1983

[54] HETEROCYCLIC AMIDES OF PHENOXYPHENOXYALKANOIC ACIDS

[75] Inventor: Takeo Hokama, Chicago, Ill.

[73] Assignee: Velsicol Chemical Corporation, Chicago, Ill.

[21] Appl. No.: 376,097

[22] Filed: May 7, 1982

[51] Int. Cl.$^3$ .................. A01N 43/00; C07D 317/10
[52] U.S. Cl. ........................................ 71/88; 549/373; 549/452
[58] Field of Search ............................ 71/88; 549/452

[56] References Cited

U.S. PATENT DOCUMENTS

| | | | |
|---|---|---|---|
| 3,979,437 | 9/1976 | Theissen | 71/118 |
| 4,067,996 | 1/1978 | Najer et al. | 549/452 |
| 4,106,925 | 8/1978 | Rohr et al. | 71/108 |
| 4,134,753 | 1/1979 | Hörlein et al. | 71/108 |
| 4,304,936 | 12/1981 | Rohr et al. | 71/88 |
| 4,309,210 | 1/1982 | Quadranti et al. | 71/88 |

FOREIGN PATENT DOCUMENTS 606902 10/1960 Canada .................. 549/452

Primary Examiner—Ethel G. Love
Attorney, Agent, or Firm—Robert J. Schwarz

[57] ABSTRACT

This invention discloses compounds of the formula

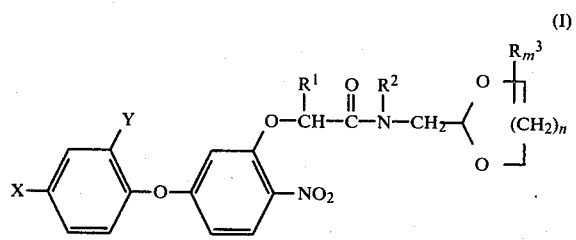

(I)

wherein X is halogen or trifluoromethyl; Y is selected from the group consisting of hydrogen, halogen, nitro and cyano; $R^1$ is alkyl; $R^2$ is selected from the group consisting of hydrogen, alkyl, alkenyl and alkynyl; and $R^3$ is selected from the group consisting of alkyl and halogen; m is an integer from 0 to 3; and n is the integer 0 or 1 and further herbicidal compositions thereof.

10 Claims, No Drawings

HETEROCYCLIC AMIDES OF PHENOXYPHENOXYALKANOIC ACIDS

This invention relates to new compositions of matter and more specifically relates to new chemical compounds of the formula:

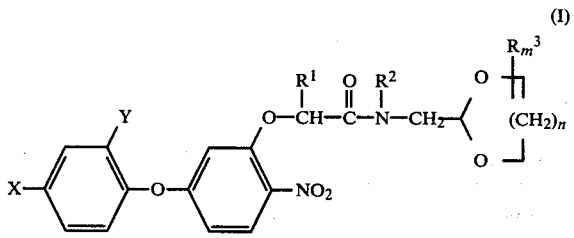

wherein X is halogen or trifluoromethyl; Y is selected from the group consisting of hydrogen, halogen, nitro and cyano; $R^1$ is alkyl; $R^2$ is selected from the group consisting of hydrogen, alkyl, alkenyl and alkynyl; and $R^3$ is selected from the group consisting of alkyl and halogen; m is an integer from 0 to 3; and n is the integer 0 or 1.

The compounds of the present invention are unexpectedly useful as selective herbicides.

In a preferred embodiment of the present invention X is chlorine, bromine or trifluoromethyl; Y is hydrogen, chlorine, bromine, nitro or cyano; $R^1$ is lower alkyl; $R^2$ is selected from the group consisting of hydrogen, lower alkyl, allyl and propargyl; $R^3$ is lower alkyl, chlorine or bromine and m and n are as heretobefore described.

In a most preferred embodiment of this invention X is trifluoromethyl and Y is chlorine.

The compounds of the present invention can be prepared by reacting an acid chloride of the formula:

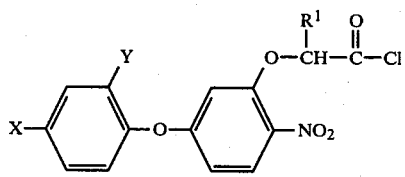

wherein X, Y and $R^1$ are as heretobefore described, with an amine of the formula:

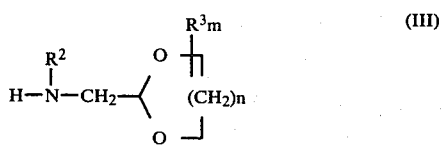

wherein $R^2$, $R^3$, m and n are as heretobefore described. This reaction can be readily effected by combining a solution of the amine of formula III with a solution of the acid chloride of formula II in an inert organic solvent such as methylene chloride, in the presence of an acid acceptor such as a tertiary amine. Typically, reaction temperatures below room temperature and those ranging from −30° C. to room temperatures are used. After the reaction is completed the reaction mixture is washed with water and/or aqueous alkali metal bicarbonate to remove acid acceptor salt and can thereafter be stripped of solvent to yield the desired product. This product can be used as such or further purified by conventional techniques.

The acid chloride of formula II can be prepared from the corresponding free acid by reaction with thionyl chloride. To effect this reaction the acid and thionyl chloride are combined with agitation in an inert, dry organic reaction medium such as toluene. The reaction can be carried out at room temperature or at elevated temperatures such as those ranging up to 90° C. After the reaction is completed the desired product can be recovered upon stripping off the solvent used as the reaction medium.

The compounds of formula II and their corresponding free acids are known in the art and are described by Schoenowsky, et. al., in Z. Naturforsch. 35b, 902–908 (1980) as well as in the European Patent Applications Nos. 0001641, published June 2, 1979, and 0011802, published June 11, 1980.

Exemplary acid precursors of the compounds of formula II useful in preparing the compounds of the present invention are: 2-[2-nitro-3-(2-chloro-4-trifluoromethylphenoxy)phenoxy]propionic acid, 2-[2-nitro-3-(4-trifluoromethylphenoxy)phenoxy]propionic acid, 2-[2-nitro-3-(2-bromo-4-trifluoromethylphenoxy)phenoxy]propionic acid, 2-[2-nitro-3-(2-nitro-4-chlorophenoxy)phenoxy]propionic acid, 2-[2-nitro-(2-cyano-4-bromophenoxy)phenoxy]propionic acid, 2-[2-nitro-3-(2,4-dichlorophenoxy)phenoxy]propionic acid, 2-[2-nitro-3-(2,4-dibromophenoxy)phenoxy]propionic acid, 2-[2-nitro-3-(4-chlorophenoxy)phenoxy]propionic acid, 2-[2-nitro-3-(4-bromophenoxy)phenoxy]propionic acid, 2-[2-nitro-3-(4-iodophenoxy)phenoxy]propionic acid, 2-[2-nitro-3-(4-fluorophenoxy)phenoxy]propionic acid.

Exemplary compounds of formula III useful in preparing the compounds of the present invention are: N-(1,3-dioxolan-2-ylmethyl)amine, N-(4-methyl-1,3-dioxolan-2-ylmethyl)amine, N-(4-ethyl-1,3-dioxolan-2-ylmethyl)amine, N-(4-propyl-1,3-dioxolan-2-ylmethyl)amine, N-(4-butyl-1,3-dioxolan-2-ylmethyl)amine, N-(4-chloro-1,3-dioxolan-2-ylmethyl)amine, N-(4-bromo-1,3-dioxolan-2-ylmethyl)amine, N-methyl-N-(1,3-dioxolan-2-ylmethyl)amine, N-ethyl-N-(1,3-dioxolan-2-ylmethyl)amine, N-propyl-N-(1,3-dioxolan-2-ylmethyl)amine, N-butyl-N-(1,3-dioxolan-2-ylmethyl)amine, N-hexyl-N-(1,3-dioxolan-2-ylmethyl)amine.

The manner in which the compounds of the present invention can be prepared is more specifically described in the following examples.

EXAMPLE 1

Preparation of 2-[2-Nitro-5-(2-chloro-4-trifluoromethylphenoxy)phenoxy]propionyl Chloride 2-[2-nitro-5-(2-chloro-4-trifluoromethylphenoxy)phenoxy]propionic acid (100 grams) and toluene (40 ml) were charged into a glass reaction vessel equipped with a magnetic stirrer. The mixture was heated on a steam bath until a solution was obtained. The solution was allowed to cool and thionyl chloride (100 ml) was added dropwise with stirring. After the addition was completed, the mixture was warmed to 67° C. with continued stirring for a period of about 2½ hours. After this time the mixture was stripped of solvent in a rotary evaporator under reduced pressure leaving as the residue 105 grams of the desired product, 2-[2-nitro-5-(2- chloro-4-trifluoromethylphenoxy)phenoxy]propionyl chloride as a burgundy colored viscous oil.

EXAMPLE 2

Preparation of N-(1,3-Dioxolan-2-ylmethyl)-2-[2-Nitro-5-(2-chloro-4-trifluoromethylphenoxy)phenoxy]propionamide N-(1,3-Dioxolan-2-ylmethyl)amine (1.85 grams; 0.015 mole), triethylamine (5 ml) and methylene chloride (50 ml) were charged into a glass reaction vessel equipped with a mechanical stirrer, thermometer and addition funnel. The mixture was cooled in a dry ice bath to a temperature of −20° C. to −10° C. and a solution of 2-[2-nitro-5-(2-chloro-4-trifluoromethylphenoxy)-phenoxy]propionyl chloride (4.2 grams; 0.01 mole) in methylene chloride (50 ml) was added dropwise with stirring. After the addition was completed the reaction mixture was allowed to warm to room temperature with stirring over a period of about 1 hour. After this time the reaction mixture was transferred to a separatory funnel and washed with water (100 ml) with dilute aqueous sodium bicarbonate (200 ml; 5% concentration) and again with water (100 ml). The washed mixture was then dried by passing it through phase separation paper and was stripped of solvent in a rotary evaporator under reduced pressure leaving a white solid residue. This residue was dissolved in toluene, treated with activated charcoal and filtered. The filtrate was partially stripped of toluene and diluted with hexane to precipitate the desired product N-(1,3-dioxolan-2-yl-methyl)-2-[2-nitro-5-(2-chloro-4-trifluoromethylphenoxy)phenoxy]propionamide as a white crystalline solid melting at 148° to 149.5° C.

EXAMPLE 3

Preparation of N-Methyl-N-(1,3-dioxolan-2-ylmethyl)-2-[2-Nitro-5-(2-chloro-4-trifluoromethylphenoxy)phenoxy]propionamide N-Methyl-N-(1,3-dixolan-2-ylmethyl)amine (1.1 grams; 0.0094 mole), triethylamine (3 ml) and toluene (60 ml) were charged into a glass reaction vessel equipped with a mechanical stirrer, thermometer and addition funnel. The reaction mixture was blanketed with nitrogen gas and a solution of 2-[2-nitro-5-(2-chloro-4-trichloromethylphenoxy)phenoxy]propionyl chloride (4.0 grams; 0.0094 mole) in toluene (50 ml) was added dropwise with stirring at room temperature. After the addition was completed the reaction mixture was stirred at room temperature overnight. After this time the mixture was transferred to a separatory funnel and was washed with water and dilute aqueous sodium bicarbonate. The washed solution was then dried, filtered and stripped of solvent leaving an orange-red gum. This gum was then subjected to chromatography using a 150 ml column filled with clay and mixtures of ethyl acetate and hexane with increasing concentrations of ethyl acetate as the eluant. A total of eleven fractions were collected. Fractions three to six were combined and stripped of solvent to yield the desired product N-methyl-N-(1,3-dioxolan-2-yl-methyl)-2-[2-nitro-5-(2-chloro-4-trifluoromethylphenoxy)phenoxy]propionamide as an orange gum.

EXAMPLE 4

Preparation of N-Ethyl-N-(1,3-dioxolan-2-ylmethyl)-2-[2-nitro-5-(2-chloro-4-trifluoromethylphenoxy)phenoxy]propionamide N-Ethyl-N-(1,3-dioxolan-2-ylmethyl)amine (1.31 grams; 0.01 mole), toluene (40 ml) and triethylamine (3 ml) were charged into a glass reaction vessel equipped with a magnetic stirrer, thermometer and addition funnel. A solution of 2-[2-nitro-5-(2-chloro-4-trifluoromethylphenoxy)phenoxy]propionyl chloride (4.2 grams; 0.01 mole) in toluene (30 ml) was added dropwise, with stirring at room temperature. A slight exotherm was observed. After the addition was completed stirring was continued for a period of about 1.5 hours. After this time the reaction mixture was transferred into a separatory funnel and was washed twice with water (60 ml), with dilute aqueous sodium bicarbonate (60 ml; 5% conc.) and again with water (60 ml). The washed organic phase was dried by passing it through phase separation paper and was thereafter stripped of solvent leaving a viscous oil as the residue. This residue was subjected to chromatography using a clay column (150 ml) and mixtures of ethyl acetate and hexane with increasing concentrations of ethyl acetate as the eluant. Nine fractions were collected. Fractions six and seven were combined and stripped of solvents to yield the desired product N-ethyl-(1,3-dioxolan-2-yl-methyl)-2-[2-nitro-5-(2-chloro-4-trifluoromethylphenoxy)phenoxy]propionamide as an amber gum.

EXAMPLE 5

Preparation of N-Propyl-N-(1,3-dioxolan-2-ylmethyl)-2-[2-nitro-5-(2-chloro-4-trifluoromethylphenoxy)phenoxy]propionamide N-n-Propyl-N-(1,3-dioxolan-2-ylmethyl)amine (1.33 grams; 0.0092 mole), dry toluene (60 ml) and triethylamine (3.0 ml) were charged into a glass reaction vessel equipped with a magnetic stirrer, thermometer and addition funnel. The reaction mixture was blanketed under nitrogen gas and a solution of 2-[2-nitro-5-(2-chloro-4-trifluoromethylphenoxy)phenoxy]propionyl chloride (3.9 grams; 0.0092 mole) in toluene (40 ml) was added dropwise with stirring. A slight exotherm was observed. After the addition was completed stirring was continued at room temperature for a period of about 1.5 hours. After this time the reaction mixture was transferred to a separatory funnel and was washed with water and dilute aqueous sodium bicarbonate. The washed solution was then dried and stripped of solvent leaving a viscous oil as the residue. This residue was then chromatographed through clay using ethyl acetate-hexane mixtures with increasing concentrations of ethyl acetate as the eluant. A total of nine fractions were collected. Fractions 5 and 6 were combined and stripped of solvents to yield the desired product N-pro pyl-N-(1,3-dioxolan-2-ylmethyl)-2-[2-nitro-5-(2-chloro-4-trifluoromethylphenoxy)phenoxy]propionamide as an amber gum.

EXAMPLE 6

Preparation of
N-Allyl-N-(1,3-dioxolan-2-ylmethyl)-2-[2-nitro-5-(2-chloro-4-trifluoromethylphenoxy)phenoxy]propionamide N-Allyl-N-(1,3-dioxolan-2-ylmethyl)amine (1.32 grams; 0.0092 mole), dry toluene (70 ml) and triethylamine (3.0 ml) were charged into a glass reaction vessel equipped with a magnetic stirrer, thermometer, gas inlet tube and addition funnel. The mixture was blanketed with nitrogen gas, cooled to 10° C. and a solution of 2-[2-nitro-5-(2-chloro-4-trifluoromethylphenoxy)-phenoxy]propionyl chloride (3.8 grams; 0.0092 mole) in toluene (40 ml) was added dropwise with stirring. After the addition was completed the mixture was allowed to warm to room temperature and stirring was continued for a period of about 1.5 hours. After this time the reaction mixture was transferred to a separatory funnel and was washed with water and with aqueous sodium bicarbonate. The washed solution was dried by passing it through phase separation paper. The dried solution was then chromatographed through a clay column using mixtures of ethyl acetate and hexane as the eluant. Nine fractions were collected. Fraction five was stripped of solvents and thereafter further dried by letting the residue stand under vacuum at 110° C. for a period of four hours to yield the desired product N-allyl-N-(1,3-dioxolan-2-ylmethyl)-2-[2-nitro-5-(2-chloro-4-trifluoromethylphenoxy)phenoxy]propionamide as an amber gum.

EXAMPLE 7

Preparation of
N-(4-Methyl-1,3-dioxolan-2-ylmethyl)-2-[2-nitro-5-(2,4-dichlorophenoxy)phenoxy]propionamide N-(4-Methyl-1,3-dioxolan-2-ylmethyl)amine (0.015 mole) triethylamine (5 ml) and methylene chloride (50 ml) are charged into a glass reaction vessel equipped with a mechanical stirrer, thermometer and addition funnel. The reaction mixture is cooled to about −15° C. and a solution of 2-[2-nitro-5-(2,4-dichlorophenoxy)-phenoxy]propionyl chloride (0.01 mole) in methylene chloride (50 ml) is added dropwise with stirring. After the addition is completed the reaction mixture is allowed to warm to room temperature with continued stirring. After this time the mixture is transferred to a separatory funnel and is washed with water and dilute aqueous sodium bicarbonate. The washed solution is then dried, filtered and stripped of solvent leaving a residue. The residue is then recrystallized from a toluene/hexane mixture to yield the desired product N-(4-methyl-1,3-dioxolan-2-ylmethyl)-2-[2-nitro-5-(2,4-dichlorophenoxy)phenoxy]propionamide.

EXAMPLE 8

Preparation of
N-Ethyl-N-(4,5-dimethyl-1,3-dioxolan-2-yl-methyl)-2-[2-nitro-5-(2-nitro-4-bromophenoxy)phenoxy]propionamide N-Ethyl-N-(4,5-dimethyl-1,3-dioxolan-2-ylmethyl)amine (0.015 mole) triethylamine (5 ml) and methylene chloride (50 ml) are charged into a glass reaction vessel equipped with a mechanical stirrer, thermometer and addition funnel. The reaction mixture is cooled to about −15° C. and a solution of 2-[2-nitro-5-(2-nitro-4-bromophenoxy)phenoxy]propionyl chloride (0.01 mole) in methylene chloride (50 ml) is added dropwise with stirring. After the addition is completed the reaction mixture is allowed to warm to room temperature with continued stirring. After this time the mixture is transferred to a separatory funnel and is washed with water and dilute aqueous sodium bicarbonate. The washed solution is then dried, filtered and stripped of solvent leaving a residue. The residue is then recrystallized from a toluene/hexane mixture to yield the desired product N-ethyl-N-(4,5-dimethyl-1,3-dioxolan-2-ylmethyl)-2-[2-nitro-5-(2-nitro-4-bromophenoxy)phenoxy]propionamide.

EXAMPLE 9

Preparation of
N-(1,3-Dioxan-2-ylmethyl)-2-[2-nitro-5-(2-cyano-4-fluorophenoxy)phenoxy]propionamide N-(1,3-Dioxan-2-ylmethyl)amine (0.015 mole) triethylamine (5 ml) and methylene chloride (50 ml) are charged into a glass reaction vessel equipped with a mechanical stirrer, thermometer and addition funnel. The reaction mixture is cooled to about −15° C. and a solution of 2-[2-nitro-5-(2-cyano-4-fluorophenoxy)-phenoxy]propionyl chloride (0.01 mole) in methylene chloride (50 ml) is added dropwise with stirring. After the addition is completed the reaction mixture is allowed to warm to room temperature with continued stirring. After this time the mixture is transferred to a separatory funnel and is washed with water and dilute aqueous sodium bicarbonate. The washed solution is then dried, filtered and stripped of solvent leaving a residue. The residue is then recrystallized from a toluene/hexane mixture to yield the desired product N-(1,3-dioxan-2-ylmethyl)-2-[2-nitro-5-(2-cyano-4-fluorophenoxy)phenoxy]propionamide.

EXAMPLE 10

Preparation of
N-(4-Chloro-1,3-dioxolan-2-ylmethyl)-2-[2-nitro-5-(4-trifluoromethylphenoxy)phenoxy]propionamide N-(4-Chloro-1,3-dioxolan-2-ylmethyl)amine (0.015 mole) triethylamine (5 ml) and methylene chloride (50 ml) are charged into a glass reaction vessel equipped with a mechanical stirrer, thermometer and addition funnel. The reaction mixture is cooled to about −15° C. and a solution of 2-[2-nitro-5-(4-trifluoromethylphenoxy)phenoxy]propionyl chloride (0.01 mole) in methylene chloride (50 ml) is added dropwise with stirring. After the addition is completed the reaction mixture is allowed to warm to room temperature with continued stirring. After this time the mixture is transferred to a separatory funnel and is washed with water and dilute aqueous sodium bicarbonate. The washed solution is then dried, filtered and stripped of solvent leaving a residue. The residue is then recrystallized from a toluene/hexane mixture to yield the desired product N-(4-chloro-1,3-dioxolan-2-ylmethyl)-2-[2-nitro-5-(4-trifluoromethylphenoxy)phenoxy]propionamide.

EXAMPLE 11

Preparation of
N-(1,3-Dioxolan-2-ylmethyl)-2-[2-nitro-5-(2-Chloro-4-trifluoromethylphenoxy)phenoxy]butyramide N-(1,3-Dioxolan-2-ylmethyl)amine (0.015 mole) triethylamine (5 ml) and methylene chloride (50 ml) are charged into a glass reaction vessel equipped with a mechanical stirrer, thermometer and addition funnel.

The reaction mixture is cooled to about −15° C. and a solution of 2-[2-nitro-5-(2-chloro-4-trifluoromethylphenoxy)phenoxy]butanoyl chloride (0.01 mole) in methylene chloride (50 ml) is added dropwise with stirring. After the addition is completed the reaction mixture is allowed to warm to room temperature with continued stirring. After this time the mixture is transferred to a separatory funnel and is washed with water and dilute aqueous sodium bicarbonate. The washed solution is then dried, filtered and stripped of solvent leaving a residue. The residue is then recrystallized from a toluene/hexane mixture to yield the desired product N-(1,3-dioxolan-2-ylmethyl)-2-[2-nitro-5-(2-chloro-4-trifluoromethylphenoxy)phenoxy]butyramide.

EXAMPLE 12

Preparation of N-Methyl-N-(1,3-dioxolan-2-ylmethyl)-2-[2-nitro-5-(2-chloro-4-trifluoromethylphenoxy)phenoxy]hexanamide N-Methyl-N-(1,3-dioxolan-2-ylmethyl)amine (0.015 mole) triethylamine (5 ml) and methylene chloride (50 ml) are charged into a glass reaction vessel equipped with a mechanical stirrer, thermometer and addition funnel. The reaction mixture is cooled to about −15° C. and a solution of 2-[2-nitro-5-(2-chloro-4-trifluoromethylphenoxy)]chloride (0.01 mole) in methylene chloride (50 ml) is added dropwise with stirring. After the addition is completed the reaction mixture is allowed to warm to room temperature with continued stirring. After this time the mixture is transferred to a separatory funnel and is washed with water and dilute aqueous sodium bicarbonate. The washed solution is then dried, filtered and stripped of solvent leaving a residue. The residue is then recrystallized from a toluene/hexane mixture to yield the desired product N-methyl-N-(1,3-dioxolan-2-ylmethyl)-2-[2-nitro-5-(2-chloro-4-trifluoromethylphenoxy)phenoxy]hexanamide.

EXAMPLE 13

Preparation of N-(4-Bromo-1,3-dioxan-2-ylmethyl)-2-[2-nitro-5-(4-fluorophenoxy)phenoxy]propionamide N-(4-Bromo-1,3-dioxan-2-ylmethyl)amine (0.015 mole) triethylamine (5 ml) and methylene chloride (50 ml) are charged into a glass reaction vessel equipped with a mechanical stirrer, thermometer and addition funnel. The reaction mixture is cooled to about −15° C. and a solution of 2-[2-nitro-5-(4-fluorophenoxy)phenoxy]propionyl chloride (0.01 mole) in methylene chloride (50 ml) is added dropwise with stirring. After the addition is completed the reaction mixture is allowed to warm to room temperature with continued stirring. After this time the mixture is transferred to a separatory funnel and is washed with water and dilute aqueous sodium bicarbonate. The washed solution is then dried, filtered and stripped of solvent leaving a residue. The residue is then recrystallized from a toluene/hexane mixture to yield the desired product N-(4-bromo-1,3-dioxan-2-ylmethyl)-2-[2-nitro-5-(4-fluorophenoxy)phenoxy]propionamide.

Additional compounds within the scope of the present invention which can be prepared by the procedures described in the foregoing examples are: N-(1,3-dioxolan-2-ylmethyl)-2-[2-nitro-5-(2-chloro-4-trifluoromethylphenoxy)phenoxy]butyramide, N-(2-methyl-1,3-dioxolan-2-ylmethyl)-2-[2-nitro-5-(2-chloro-4-trifluoromethylphenoxy)phenoxy]pentanamide, N-(1,3-dioxolan-2-ylmethyl)-2-[2-nitro-5-(2-chloro-4-trifluoromethylphenoxy)phenoxy]hexanamide, N-(1,3-dioxolan-2-ylmethyl)-2-[2-nitro-5-(2-chloro-4-trifluoromethylphenoxy)phenoxy]octanamide, N-(1,3-dioxolan-2-ylmethyl)-2-[2-nitro-5-(2-chloro-4-trifluoromethylphenoxy)phenoxy]propionamide, N-(4-ethyl-1,3-dioxolan-2-ylmethyl)-2-[2-nitro-5-(2-chloro-4-trifluoromethylphenoxy)phenoxy]propionamide, N-(4-butyl-1,3-dioxolan-2-ylmethyl)-2-[2-nitro-5-(2-chloro-4-trifluoromethylphenoxy)phenoxy]propionamide, N-(4-propyl-1,3-dioxolan-2-ylmethyl)-2-[2-nitro-5-(2-chloro-4-trifluoromethylphenoxy)phenoxy]propionamide, N-(4-hexyl-1,3-dioxolan-2-ylmethyl)-2-[2-nitro-5-(2-bromo-4-trifluoromethylphenoxy)phenoxy]propionamide, N-propyl-N-(5-methyl-1,3-dioxan-2-ylmetnyl)-2-[2-nitro-5-(2-chloro-4-trifluoromethylphenoxy)phenoxy]propionamide, N-butyl-N-(2-methyl-1,3-dioxan-2-ylmethyl)-2-[2-nitro-5-(2-chloro-4-trifluoromethylphenoxy)phenoxy]propionamide, N-hexyl-N-(5-methyl-1,3-dioxan-2-ylmethyl)-2-[2-nitro-5-(2-chloro-4-trifluoromethylphenoxy)phenoxy]propionamide, N-methyl-N-(4-chloro-5-ethyl-1,3-dioxan-2-ylmethyl)-2-[2-nitro-5-(2-chloro-4-trifluoromethylphenoxy)phenoxy]propionamide, N-methyl-N-(1,3-dioxan-2-ylmethyl)-2-[2-nitro-5-(2-chloro-4-trifluoromethylphenoxy)phenoxy]pentanamide, N-methyl-N-(1,3-dioxan-2-ylmethyl)-2-[2-nitro-5-(2-chloro-4-trifluoromethylphenoxy)phenoxy]hexanamide, N-methyl-N-(1,3-dioxan-2-ylmethyl)-2-[2-nitro-5-(2-chloro-4-dioxolan-2-ylmethyl)]-2-[2-nitro-5-(2-nitro-4-chlorophenoxy)phenoxy]butyramide, N-methyl-N-(1,3-dioxolan-2-ylmethyl)-2-[2-nitro-5-(2-cyano-4-chlorophenoxy)phenoxy]butyramide.

For practical use as herbicides the compounds of this invention are generally incorporated into herbicidal compositions which comprise an inert carrier and a herbicidally toxic amount of such a compound. Such herbicidal compositions, which can also be called formulations, enable the active compound to be applied conveniently to the site of the weed infestation in any desired quantity. These compositions can be solids such as dusts, granules, or wettable powders; or they can be liquids such as solutions, aerosols or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under superatmospheric pressure as aerosols. However, preferred liquid herbicidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water in oil) can be prepared for direct application to weed infestations.

A typical herbicidal composition according to this invention is illustrated by the following example, in which the quantities are in parts by weight.

EXAMPLE 14

Preparation of a Dust

| Product of Example 2 | 10 |
|---|---|
| Powdered Talc | 90 |

The above ingredients are mixed in a mechanical grinder-blender and are ground until a homogeneous, free-flowing dust of the desired particle size is obtained. This dust is suitable for direct application to the site of the weed infestation.

The compounds of this invention can be applied as herbicides in any manner recognized by the art. One method for the control of weeds comprises contacting the locus of said weeds with a herbicidal composition comprising an inert carrier and as an essential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about 0.05 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers, spreaders, deactivators, adhesives, stickers, fertilizers, activators, synergists and the like.

The compounds of the present invention are also useful when combined with other herbicides and/or defoliants, dessicants, growth inhibitors and the like in the herbicidal compositions heretobefore described. These other materials can comprise from about 5% to about 95% of the active ingredients in the herbicidal compositions. Use of combinations of these other herbicides and/or defoliants, dessicants, etc. with the compounds of the present invention provide herbicidal compositions which are more effective in controlling weeds and often provide results unattainable with separate compositions of the individual herbicides. The other herbicides, defoliants, dessicants and the plant growth inhibitors, with which the compounds of this invention can be used in the herbicidal compositions to control weeds, can include chlorophenoxy herbicides such as 2,4-D, 2,4,5-T, MCPA, MCPB, 4(2,4-DB), 2,4-DEB, 4-CPB, 4-CPP, 2,4,5-TB, 2,4,5-TES, 3,4-DA, silvex and the like; carbamate, herbicides such as IPC, CIPC, swep, barban, BCPC, CEPC, CPPC, and the like; thiocarbamate and dithiocarbamate herbicides such as DCEC, methan sodium, EPTX, diallate, PEBC, perbulate, vernolate and the like; substituted urea herbicides such as norea, siduron, dichloral urea, chloroxuron, cycluron, fenuron, monuron, monuron TCA, diuron, linuron, monolinuron, neburon, buturon, trimeturon and the like; symmetrical triazine, herbicides such as simazine, chlorazine, atraone, desmetryne, norazine, ipazine, prometryn, atrazine, trietazine, simetone, prometone, propazine, ametryne, and the like; chloroacetamide herbicides such as alpha-chloro-N,N-dimethylacetamide, CDEA, CDAA, alpha-chloro-N-isopropylacetamide, 2-chloro-N-isopropylacetanilide, 4-(chloroacetyl)-morpholine, 1-(chloroacetyl) piperidine, and the like; chlorinated aliphatic acid herbicides such as TCA, dalapon, 2,3-dichloropropionic acid, 2,2,3-TPA and the like; chlorinated benzoic acid and the phenylacetic acid herbicides such as 2,3,6-TBA, 2,3,5,6-TBA, dicamba, tricamba, amiben, fenac, PBA, 2-methoxy-3,6-dichlorophenylacetic acid, 3-methoxy-2,6-dichlorophenylacetic acid, 2-methoxy-3,4,6-trichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlorobenil, DPA, diphenamid, dipropalin, trifluraline, solan, dicryl, merphos, DMPA, DSMA, MSMA, potassium azide, acrolein, benefin, bensulide, AMS, bromacil, 2-(3,4-dichlorophenyl)-4-methyl-1,2,4-oxadiazolidine, 3,5-dione, bromoxynil, cacodylic acid, DMA, DPMF, cypromid, DCB, DCPA, dichlone, diphenatril, DMTT, DNAP, EBEP, EXD, HCA, ioxynil, IPX, isocyil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-732, M-2091, planavin, sodium tetraborate, calcium cyanamid, DEF, ethyl xanthogen disulfide, sindone, sindone B, propanil and the like.

Such herbicides can also be used in the methods and composition of this invention in the form of their salts, esters, amides, and other derivatives whenever applicable to the particular parent compounds.

Weeds are undesirable plants growing where they are not wanted; having no economic value, and interfering with the production of cultivated crops, with the growing of ornamental plants, or with the welfare of livestock. Many types of weeds are known, including annuals such as pigweed, lambsquarter, foxtail, crabgrass, wild mustard, field pennycress, ryegrass, goose grass, chickweed, wild oats, velvet leaf, purselane, barnyard grass, smartweed, knotweed, cocklebur, wild buckwheat, kochia, medic corn cockle, ragweed, sowthistle, coffee-weed, croton, cuphea, dodder, fumitory, groundsel, hemp nettle, knowel, spurge, spurry, emex, jungle rice, pondweed, dog fennel, carpetweed, morning glory, bedstraw, ducksalad and naiad; biennials such as wild carrot, matricaria, wild barley, campion, chamomile, burdock, mullein, roundleaved mallow, bull thistle, hounds-tongue, moth mullein, and purple star thistle; or perennials such as white cockle, perennial ryegrass, quackgrass Johnson grass, Canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cattail and wintercress.

Similarly, such weeds can be classified as broadleaf or grassy weeds. It is economically desirable to control the growth of such weeds without damaging beneficial plants or livestock.

The new compounds of this invention are particularly valuable for weed control because they are toxic to many species and groups of weeds while they are relatively nontoxic to many beneficial plants. The exact amount of compound required will depend on a variety of factors, including the hardiness of the particular weed species, weather, type of soil, method of application, the kind of beneficial plants in the same area, and the like. Thus, while the application of up to only about one or two ounces of active compound per acre may be sufficient for good control of a light infestation of weeds growing under adverse conditions, the application of ten pounds or more of active compound per acre may be required for good control of a dense infestation of hardy perennial weeds growing under favorable conditions.

The herbicidal toxicity of the new compounds of this invention can be illustrated by many of the established testing techniques known to the art, such as pre- and post-emergence testing.

The herbicidal activity of the compounds of this invention was demonstrated by experiments carried out for the pre-emergence control of a variety of weeds. In these experiments small plastic greenhouse pots filled with dry soil were seeded with the various weed seeds. Twenty-four hours or less after the seeding, the pots were sprayed with water until the soil was wet and the test compounds formulated as aqueous emulsions of acetone solutions containing emulsifiers were sprayed at the indicated concentrations on the surface of the soil.

After spraying, the soil containers were placed in the greenhouse and provided with supplementary heat as required and daily or more frequent watering. The plants were maintained under these conditions for a period of from 15 to 21 days, at which time the condition of the plants and the degree of injury to the plants was rated on a scale of from 0 to 10, as follows: 0=no injury, 1, 2=slight injury, 3, 4=moderate injury, 5, 6=moderately severe injury, 7, 8, 9=severe injury, 10=death and NE indicated not emerged. The effectiveness of these compounds is demonstrated by the following data set out in Table I. Numbers with decimal places are the result of averaging two or more ratings obtained from replicate experiments.

The herbicidal activity of the compounds of this invention was also demonstrated by experiments carried out for the post-emergence control of a variety of weeds. In these experiments the compounds to be tested were formulated as aqueous emulsions and sprayed at the indicated dosage on the foliage of the various weed species that have attained a prescribed size. After spraying, the plants were placed in a greenhouse and watered daily or more frequently. Water was not applied to the foliage of the treated plants. the severity of the injury was determined 10 to 15 days after treatment and was rated on the scale of from 0 to 10 heretobefore described. The effectiveness of these compounds is demonstrated by the following data set forth in Table II. Values which decimal places again are the result of averaging of replicate experiments.

TABLE I

14 & 21-Day Primary, Secondary & Advanced PRE-EMERGENCE SCREEN

| | Compound: Product of Example 2 | | | | | | | | | | Compound: Product of Example 3 | | | | | | | |
|---|---|---|---|---|---|---|---|---|---|---|---|---|---|---|---|---|---|---|
| #/Acre: | 8 | | 1 | | .5 | | .25 | | .125 | | 1 | | .5 | | .25 | | .125 | |
| | 14 | 21 | 14 | 21 | 14 | 21 | 14 | 21 | 14 | 21 | 14 | 21 | 14 | 21 | 14 | 21 | 14 | 21 |
| WMSD | NE | NE | 10 | 10 | 10 | 10 | 0 | 10 | 10 | 10 | 10 | 10 | 10 | 10 | 9 | 9 | 5 | 0 |
| BDWD | — | — | 9 | 10 | 8 | 7 | 3 | 4 | 3 | 4 | 9 | 10 | 10 | 10 | 7 | 5 | 5 | 0 |
| PIGW | 10 | 10 | 10 | 10 | NE | NE | NE | NE | 10 | 10 | NE | NE | NE | NE | NE | NE | NE | NE |
| JMWD | NE | NE | NE | NE | NE | NE | NE | NE | NE | NE | NE | NE | NE | NE | NE | NE | NE | NE |
| VTLF | NE | NE | NE | 10 | 10 | 10 | 10 | 10 | 9 | 10 | 10 | 10 | 10 | 10 | 2 | 0 | 2 | 0 |
| MNGY | 8 | 9 | 2 | 1 | 2 | 1 | 3 | 2 | 3 | 2 | 9 | 10 | 9 | 7 | 2 | 2 | 0 | 0 |
| YLFX | 10 | 10 | 8 | 7 | 6 | 6 | 5 | 3 | 5 | 3 | NE | 10 | 9 | 9 | 7 | 0 | 0 | 0 |
| BNGS | NE | NE | 10 | 10 | 8 | 8 | 7 | 8 | 4 | 4 | 10 | 10 | 9 | 10 | 2 | 0 | 3 | 0 |
| JNGS | NE | NE | 10 | 10 | NE | 10 | 10 | 10 | 4 | 6 | 10 | 10 | 10 | 10 | 7 | 5 | 2 | 0 |
| QKGS | — | — | 9 | 10 | 4 | 6 | 0 | 2 | 0 | 0 | NE | NE | NE | 5 | 2 | 0 | 0 | 5 |
| WOAT | 10 | 10 | 6 | 4 | 7 | 8 | 4 | 3 | 0 | 0 | 10 | 10 | 10 | 5 | 0 | 0 | 0 | 0 |
| CBGS | NE | NE | NE | NE | 10 | 10 | NE | 10 | 4 | 3 | NE | NE | NE | NE | 9 | 9 | 8 | 5 |
| SPGT | — | — | 10 | 10 | NE | NE | NE | NE | 2 | 3 | NE | NE | NE | NE | 8 | 0 | 6 | 0 |
| CTGS | NE | NE | 3 | 2 | 5 | 6 | 4 | 2 | 0 | 0 | NE | NE | NE | 5 | 4 | 8 | 9 | 0 |
| SUBT | — | — | 10 | 10 | 10 | 10 | 10 | 10 | 10 | 10 | NE | NE | 10 | 10 | 9 | 10 | 10 | 10 |
| SOYB | — | — | 10 | 10 | 9 | 10 | 6 | 6 | 0 | 1 | 7 | 6 | 0 | 0 | 0 | 0 | 0 | 0 |
| COTN | — | — | 1 | 1 | 1 | 0 | 0 | 0 | 0 | 0 | 5 | 2 | 1 | 0 | 0 | 0 | 0 | 0 |
| PTBN | — | — | 10 | 10 | 10 | 10 | 10 | 10 | 6 | 6 | 10 | 10 | 10 | 10 | 6 | 6 | 5 | 6 |
| ALFA | — | — | 10 | 10 | 10 | 10 | 10 | 10 | 6 | 4 | 10 | 10 | 10 | 10 | 10 | 10 | 0 | 6 |
| WHT | — | — | 8 | 10 | 7 | 7 | 5 | 4 | 2 | 0 | 9 | 10 | 7 | 9 | 2 | 0 | 1 | 0 |
| RICE | — | — | 1 | 1 | 1 | 0 | 1 | 0 | 0 | 0 | 8 | 7 | 6 | 2 | 4 | 0 | 0 | 0 |
| SORG | — | — | 9 | 10 | 9 | 10 | 3 | 3 | 4 | 3 | 10 | 10 | 10 | 9 | 8 | 7 | 1 | 0 |
| CORN | — | — | 6 | 6 | 4 | 4 | 5 | 4 | 5 | 4 | 9 | 9 | 9 | 5 | 4 | 0 | 3 | 3 |
| OAT | — | — | 7 | 10 | 10 | 10 | 1 | 3 | 0 | 0 | 10 | 10 | 10 | 9 | 2 | 0 | 6 | 1 |
| YNSG | NE | NE | — | — | — | — | — | — | — | — | — | — | — | — | — | — | — | — |

| | Compound: Product of Example 4 | | | | | | | | | | | | Compound: Product of Example 5 | | | | |
|---|---|---|---|---|---|---|---|---|---|---|---|---|---|---|---|---|---|
| #/Acre: | 4 | | 2 | | 1 | | .5 | | .25 | | .125 | | 4 | | 2 | | 1 | |
| | 14 | 21 | 14 | 21 | 14 | 21 | 14 | 21 | 14 | 21 | 14 | 21 | 14 | 21 | 14 | 21 | 14 | 21 |
| WMSD | NE | NE | NE | NE | 10* | 10* | NE | NE | 9 | 10 | 7 | 10 | 10* | 9.5* | 4 | 0 | 4 | 0 |
| BDWD | — | — | — | — | 6 | 10 | 1 | 7 | — | — | — | — | — | — | — | 7 | — | — |
| PIGW | 10 | 10 | 10 | 10 | 10* | 10* | 6.5* | 10* | 8* | 7* | 2 | 10 | 10* | 10* | 8 | 7 | 10 | 10 |
| JMWD | NE | NE | NE | NE | NE | NE | NE | NE | NE | NE | NE | NE | 10* | 10* | 10 | 10 | 9 | 10 |
| VTLF | 9 | 10 | 9 | 10 | NE | NE | NE | NE | NE | NE | 10 | 10 | 10* | 10* | 6 | 3 | 6 | 3 |
| MNGY | 10 | 10 | 5 | 3 | 4.5* | 7 | 10 | 10 | 7 | 6 | 3 | 0 | 0 | 0 | 0 | 0 | 0 | 0 |
| YLFX | 10 | 10 | 9 | 7 | 10* | 10* | 10 | 10 | 1 | 0 | 1 | 0 | 1 | 0 | 0 | 0 | 0 | 0 |
| BNGS | 10 | 10 | NE | NE | 10* | 10* | 10 | 9 | 7 | 7 | 4 | 4 | 9* | 9* | 5 | 3 | 6 | 6 |

TABLE I-continued

14 & 21-Day Primary, Secondary & Advanced PRE-EMERGENCE SCREEN

| | | | | | | | | | | | | | | | | | | |
|---|---|---|---|---|---|---|---|---|---|---|---|---|---|---|---|---|---|---|
| JNGS | 9 | 10 | 10 | 10 | 9.5* | 9.5* | 10 | 8 | 8 | 9 | 5 | 6 | 10* | 10* | 6 | 5 | 7 | 5 |
| QKGS | — | — | — | — | NE | 8 | 5 | 6 | 4 | 3 | 0 | 0 | — | — | — | — | — | — |
| WOAT | 7 | 10 | 5 | 4 | 5* | 5.5* | 4 | 10 | 4 | 10 | 0 | 7 | 2* | 1* | 0 | 0 | 0 | 0 |
| CBGS | NE | NE | 7 | 7 | 7* | 7* | 8 | 10 | NE | NE | 2 | 7 | 1 | 0 | 1 | 0 | 0 | 0 |
| SPGT | — | — | — | — | 10 | 10 | 10 | 10 | 10 | 10 | 6 | 3 | — | — | — | — | — | — |
| CTGS | 3 | 3 | 3 | 3 | 5 | 6.5* | 6 | 10 | 0 | 10 | 0 | 0 | 1 | 8 | 0 | 0 | 0 | 0 |
| SUBT | — | — | — | — | 10 | 10 | 10 | 10 | 10 | 10 | 10 | 10 | | | | | | |
| COTN | — | — | — | — | 7 | 7 | 6 | 5 | 0 | 2 | 0 | 2 | | | | | | |
| SOYB | — | — | — | — | 8 | 10 | 10 | 10 | 6 | 10 | 3 | 10 | | | | | | |
| PTBN | — | — | — | — | 10 | 10 | 10 | 10 | 7 | 1 | 4 | 4 | | | | | | |
| ALFA | — | — | — | — | 10 | 10 | NE | NE | 10 | 10 | 8 | 6 | | | | | | |
| SORG | — | — | — | — | 7 | 10 | 10 | 10 | NE | 5 | 2 | 3 | | | | | | |
| WHT | — | — | — | — | 5 | 8 | NE | NE | 2 | 10 | 0 | 4 | | | | | | |
| RICE | — | — | — | — | 10 | 5 | 10 | 7 | 7 | 4 | 0 | 1 | | | | | | |
| CORN | — | — | — | — | 6 | 6 | 6 | 5 | 4 | 3 | 2 | 0 | | | | | | |
| OAT | — | — | — | — | 4 | 10 | 4 | 8 | 3 | 10 | 2 | 3 | | | | | | |
| YNSG | 0 | 0 | 0 | 0 | 0 | 0 | — | — | — | — | — | — | 2 | 2 | 0 | 0 | 0 | 0 |

| | Compound: Product of Example 6 | | | | | | |
|---|---|---|---|---|---|---|---|
| #/Acre: | 1 | | .5 | | .25 | | .125 |
| | 14 | 21 | 14 | 21 | 14 | 21 | 14 | 21 |
| WMSD | 10 | 10 | 10 | 10 | 6 | 10 | 5 | 6 |
| BDWD | 2 | 8 | 3 | 6 | 2 | 0 | 0 | 0 |
| PIGW | 10 | 10 | 10 | 10 | 10 | 10 | 0 | 0 |
| JMWD | NE | 9 | NE | NE | 9 | 9 | 7 | 0 |
| VTLF | NE | NE | NE | 4 | 10 | 10 | NE | NE |
| MNGY | 4 | 7 | 4 | 7 | 3 | 3 | 0 | 0 |
| YLFX | 6 | 6 | 6 | 3 | 0 | 0 | 0 | 0 |
| BNGS | 7 | 10 | 6 | 9 | 0 | 0 | 3 | 0 |
| JNGS | 10 | 10 | 6 | 7 | 6 | 7 | 4 | 5 |
| QKGS | 6 | 3 | 3 | 0 | 0 | 0 | 0 | 0 |
| WOAT | 8 | 10 | 5 | 3 | 0 | 3 | 0 | 0 |
| CBGS | NE | 10 | 9 | 0 | 0 | 0 | 0 | 0 |
| SPGT | 10 | 10 | 10 | 0 | 2 | 0 | 0 | 0 |
| CTGS | 6 | 8 | 5 | 0 | 0 | 0 | 0 | 0 |
| SUBT | 10 | 10 | 10 | 10 | 4 | 7 | 0 | 0 |
| SOYB | 7 | 10 | 7 | 10 | 0 | 0 | 0 | 0 |
| COTN | 3 | 4 | 3 | 4 | 0 | 0 | 0 | 0 |
| PTBN | 10 | 10 | 8 | 0 | 3 | 0 | 0 | 0 |
| ALFA | 10 | 10 | 10 | 10 | 10 | 10 | 0 | 0 |
| WHT | 3 | 5 | 3 | 10 | 0 | 0 | 0 | 0 |
| RICE | 4 | 3 | 4 | 2 | 0 | 0 | 0 | 0 |
| SORG | 8 | 10 | 6 | 0 | 1 | 0 | 0 | 0 |
| CORN | 0 | 0 | 0 | 0 | 0 | 0 | 0 | 0 |
| OAT | 6 | 10 | 5 | 0 | 0 | 0 | 0 | 0 |
| YNSG | — | — | — | — | — | — | — | — |

*Average of two or more tests

TABLE II

Primary, Secondary & Advanced POST-EMERGENCE SCREEN

| | Compound: Product of Example 2 | | | | | Compound: Product of Example 3 | | | | Compound: Product of Example 4 | | | | | | | Compound: Product of Example 5 | Compound: Product of Example 6 | | | |
|---|---|---|---|---|---|---|---|---|---|---|---|---|---|---|---|---|---|---|---|---|---|
| #/Acre: | 8 | 1 | .5 | .25 | .125 | 1 | .5 | .25 | .125 | 8 | 4 | 2 | 1 | .5 | .25 | .125 | 4 | 1 | .5 | .25 | .125 |
| WMSD | 10 | 10* | 10* | 10* | 8.5* | 10 | 10 | 10 | 7 | 10 | 10 | 10 | 10* | 10 | 10 | 10 | 10 | 10 | 10 | 10 | 10 |
| BDWD | 10 | 9.5* | 6* | 3.5* | 10* | 9 | 2 | 2 | 0 | 10 | 10 | 10 | 10* | 9 | 3 | 0 | 4 | 8 | 3 | 0 | 0 |
| PIGW | — | 10* | 10* | 10* | 9.5* | — | 10 | 10 | 9 | — | — | — | 10* | 10 | 10 | 10 | — | 10 | 10 | 10 | 10 |
| JMWD | 10 | 10* | 10* | 10* | 10* | 10 | 10 | 10 | 10 | 10 | 10 | 10 | 10* | 10 | 10 | 10 | 6 | 10 | 10 | 10 | 10 |
| VTLF | — | 10* | 10* | 10 | 10* | 10 | 10 | 10 | 10 | — | — | — | 10 | 10 | 10 | 10 | — | 10 | 10 | 10 | 10 |
| MNGY | 10 | 10* | 6.5* | 10* | 10* | 10 | 3 | 0 | 0 | 7 | 8 | 10 | 8.5* | 8 | 2 | 1 | 6 | 5 | 4 | 4 | 2 |
| YLFX | 10 | 9* | 7.5* | 8.5* | 10* | 8 | 5 | 7 | 0 | 10 | 10 | 8 | 6* | 7 | 0 | 0 | 6 | 1 | 0 | 0 | 0 |
| BNGS | 10 | 10* | 9.5* | 8.5* | 10* | 10 | 9 | 7 | 0 | 10 | 10 | 10 | 10* | 10 | 1 | 0 | 8 | 3 | 2 | 0 | 0 |
| JNGS | 10 | 10* | 10* | 10* | 5.5* | 10 | 10 | 10 | 1 | 10 | 10 | 10 | 10* | 10 | 10 | 9 | 10 | 9 | 5 | 10 | 0 |
| QKGS | — | 10* | 8.5* | 6* | 4* | 10 | 7 | 2 | 0 | — | — | — | 9 | 1 | 0 | 0 | — | 0 | 0 | 0 | 0 |
| WOAT | 10 | 7.5* | 10* | 2* | 3* | 5 | 0 | 0 | 0 | 10 | 10 | 10 | 8.5* | 10 | 10 | 2 | 1 | 10 | 0 | 8 | 2 |
| CBGS | 10 | 9* | 10* | 10* | 10* | 8 | 10 | 0 | 0 | 10 | 10 | 10 | 8.5* | 10 | 10 | 9 | 10 | 10 | 9 | 10 | 8 |
| SPGT | — | 10* | 10* | 10* | 10* | 10 | 10 | 10 | 10 | — | — | — | 10 | 10 | 10 | 10 | — | 10 | 10 | 10 | 3 |
| CTGS | — | 6* | 5* | 0* | 0* | 2 | 0 | 0 | 0 | — | — | — | 0 | 0 | 0 | 0 | | 0 | 0 | 0 | 0 |
| SUBT | — | 10* | 10* | 10* | 10* | 10 | 10 | 10 | 10 | — | — | — | 10 | 10 | 10 | 10 | | 10 | 10 | 10 | 10 |
| COTN | — | 10* | 10* | 10* | 10* | 10 | 10 | 10 | 10 | — | — | — | 10 | 10 | 10 | 10 | | 10 | 10 | 10 | 8 |
| SOYB | 9 | 6* | 5* | 7* | 5* | 5 | 3 | 0 | 0 | 7 | 7 | 6 | 6* | 8 | 5 | 3 | 3 | 2 | 1 | 0 | 0 |
| PTBN | — | 10* | 10* | 10* | 8* | 10 | 10 | 10 | 10 | — | — | — | 10 | 10 | 10 | 9 | | 8 | 7 | 7 | 2 |
| ALFA | — | 10* | 10* | 10* | 10* | 10 | 10 | 10 | 10 | — | — | — | 10 | 10 | 10 | 10 | | 10 | 10 | 10 | 5 |
| SORG | — | 10* | 10* | 8* | 7* | 10 | 10 | 8 | 7 | — | — | — | 10 | 7 | 2 | 1 | | 4 | 1 | 0 | 0 |

TABLE II-continued

Primary, Secondary & Advanced
POST-EMERGENCE SCREEN

| #/Acre: | Compound: Product of Example 2 | | | | | Compound: Product of Example 3 | | | | Compound: Product of Example 4 | | | | | | | Compound: Product of Example 5 | Compound: Product of Example 6 | | | |
|---|---|---|---|---|---|---|---|---|---|---|---|---|---|---|---|---|---|---|---|---|---|
| | 8 | 1 | .5 | .25 | .125 | 1 | .5 | .25 | .125 | 8 | 4 | 2 | 1 | .5 | .25 | .125 | 4 | 1 | .5 | .25 | .125 |
| WHT | — | 3.5* | 5.5* | 0* | 0* | 5 | 1 | 0 | 0 | — | — | — | 10 | 9 | 3 | 0 | 2 | 1 | 0 | 0 |
| RICE | — | 5.5* | 4* | 2* | 0* | 8 | 5 | 2 | 0 | — | — | — | 0 | 0 | 0 | 0 | 0 | 0 | 0 | 0 |
| CORN | — | 8* | 7.5* | 5.5* | 5* | 6 | 7 | 1 | 0 | — | — | — | 7 | 3 | 0 | 0 | 0 | 0 | 0 | 0 |
| OAT | — | 10* | 5.5* | 7* | 3* | 10 | 1 | 0 | 0 | — | — | — | 10 | 10 | 10 | 10 | 10 | 5 | 10 | 2 |
| YNSG | 7 | — | — | — | — | — | — | — | — | 0 | 0 | 0 | 0 | — | — | — | 0 | — | — | — | — |

*Average of two or more tests

ABBREVIATIONS FOR WEEDS & CROPS
WMSD = Wild Mustard
BDWD = Bindweed
PIGW = Pigweed
JMWD = Jimsonweed
VTLF = Velvetleaf
MNGY = Morningglory
YLFX = Yellow Foxtail
BNGS = Barnyardgrass
JNGS = Johnsongrass
QKGS = Quickgrass
WOAT = Wild Oat
CBGS = Crabgrass
SPGT = Sprangletop
CTGS = Cheatgrass
SUBT = Sugarbeet
SOYB = Soybean
COTN = Cotton
PTBN = Pintobean
ALFA = Alfalfa
WHT = Wheat
SORG = Surgum
YNSG = Yellow Nutsedge

I claim:

1. A compound of the formula:

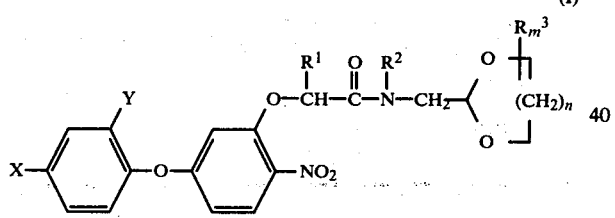

(I)

wherein X is halogen or trifluoromethyl; Y is selected from the group consisting of hydrogen, halogen, nitro and cyano; $R^1$ is alkyl; $R^2$ is selected from the group consisting of hydrogen, alkyl, alkenyl and alkynyl; and $R^3$ is selected from the group consisting of alkyl and halogen; m is an integer from 0 to 3; and n is the integer 0.

2. The compound of claim 1, N-(1,3-dioxolan-2-ylmethyl)-2-[2-nitro-5-(2-chloro-4-trifluoromethylphenoxy)-phenoxy]propionamide.

3. The compound of claim 1, N-methyl-N-(1,3-dioxolan-2-ylmethyl)-2-[2-nitro-5-(2-chloro-4-trifluoromethylphenoxy)phenoxy]propionamide.

4. The compound of claim 1, N-ethyl-N-(1,3-dioxolan-2-ylmethyl)-2-[2-nitro-5-(2-chloro-4-trifluoromethylphenoxy)phenoxy]propionamide.

5. The compound of claim 1, N-propyl-N-(1,3-dioxolan-2-ylmethyl)-2-[2-nitro-5-(2-chloro-4-trifluormethylphenoxy)phenoxy]propionamide.

6. The compound of claim 1, N-allyl-N-(1,3-dioxolan-2-ylmethyl)-2-[2-nitro-5-(2-chloro-4-trifluoromethylphenoxy)phenoxy]propionamide.

7. The compound of claim 1, N-(4-chloro-1,3-dioxolan-2-ylmethyl)-2-[2-nitro-5-(4-trifluoromethylphenoxy)-6-nitrophenoxy]propionamide.

8. The compound of claim 1, N-(1,3-dioxolan-2-ylmethyl)-2-[3-(2-chloro-4-trifluoromethylphenoxy)-6-nitrophenoxy]butyramide.

9. A herbicidal composition comprising an inert carrier and, in a quantity toxic to weeds a compound of claim 1.

10. A method of controlling weeds which comprises contacting said weeds or the locus of said weeds with a herbicidal composition of claim 9.

* * * * *